(12) United States Patent
Yu et al.

(10) Patent No.: US 8,277,855 B2
(45) Date of Patent: Oct. 2, 2012

(54) METHOD OF CONTINUOUSLY PRODUCING EDIBLE LIPID-BASED COMPOSITION

(75) Inventors: Zer-Ran Yu, Chiayi (TW); Be-Jen Wang, Chiayi (TW)

(73) Assignees: Shuen-An Kang, Taichung (TW); Zer-Ran Yu, Chiayi (TW)

( * ) Notice: Subject to any disclaimer, the term of this patent is extended or adjusted under 35 U.S.C. 154(b) by 336 days.

(21) Appl. No.: 12/776,091

(22) Filed: May 7, 2010

(65) Prior Publication Data
US 2011/0274784 A1 Nov. 10, 2011

(51) Int. Cl.
*A23L 1/48* (2006.01)
*C12N 1/00* (2006.01)
(52) U.S. Cl. .......................................... 426/7; 435/255.4
(58) Field of Classification Search .... 426/7; 435/255.4
See application file for complete search history.

(56) References Cited

U.S. PATENT DOCUMENTS
7,998,712 B2 * 8/2011 Sumida et al. ................ 435/134
* cited by examiner

*Primary Examiner* — Herbert J Lilling
(74) *Attorney, Agent, or Firm* — Ming Chow; Sinorica, LLC

(57) ABSTRACT

The present invention provides a method of continuously producing edible lipid-based composition, including the steps: preparing alcohol and organic acid in a predetermined ratio and a reaction tank received with immobilized *candida cylindracea*; continuously providing a supercritical state solvent into the reaction tank and draining the supercritical state solvent out, and mixing and pressurizing the alcohol and the organic acid and sending the alcohol and the organic acid to the reaction tank for a esterfication of the alcohol and the organic acid by the *candida cylindracea*; getting an edible lipid-based composition and water in the reaction tank; and quickly separating the edible lipid-based composition from the water and the supercritical state solvent.

11 Claims, 5 Drawing Sheets

METHOD OF CONTINUOUSLY PRODUCING EDIBLE LIPID-BASED COMPOSITION

BACKGROUND OF THE INVENTION

1. Field of the Invention

The present invention relates generally to an edible lipid-based composition, and more particularly to a method of continuously producing edible lipid-based composition.

2. Description of the Related Art

Typically, the effective component of propolis is caffeic acid phenethyl ester (CAPE) to serve the functions of anti-inflamatory, antiviral, immunostimulatory, and carcinostatic activities.

A conventional method of producing CAPE is extracting it by an organic solution. However, this method is very expensive. It costs about 50,000 NT dollars for extracting a gram of CAPE (it is calculated by extracting 0.1 g of CAPE from a kilogram). According to the related reports, 5-20 mg/mL CAPE solution is effective in treatment. In other words, it needs at least 1,000 NT dollars CAPE for treatment.

A better method is using supercritical fluid technique to produce CAPE by enzymatic esterification that the CAPE has no residual solution and is cheaper. The conventional technique is using supercritical state carbon dioxide ($SC-CO_2$) as a solution for esterification with *candida cylindracea*. This indicates that *candida cylindracea* advantages over the synthesis of lipid-base composition of low-carbon-chain fatty acids (C4~C8). However, there is no technique using enzymatic transesterification to produce CAPE by enzyme esterification.

SUMMARY OF THE INVENTION

The primary objective of the present invention is to provide a method of continuously producing edible lipid-based composition, which continuously produces edible lipid-based composition, such as alcohol, caffeic acid phenethyl ester, and lipid. The method of the present invention has a high speed production, no residual solvent, and lower cost.

According to the objective of the present invention, a method of continuously producing edible lipid-based composition includes the steps: preparing alcohol and organic acid in a predetermined ratio and a reaction tank received with immobilized *candida cylindracea*; continuously providing a supercritical state solvent into the reaction tank and draining the supercritical state solvent out, and mixing and pressurizing the alcohol and the organic acid and sending the alcohol and the organic acid to the reaction tank for a esterfication of the alcohol and the organic acid by the *candida cylindracea*; getting an edible lipid-based composition and water in the reaction tank; and quickly separating the edible lipid-based composition from the water and the supercritical state solvent.

DETAILED DESCRIPTION OF THE INVENTION

Figure 1:
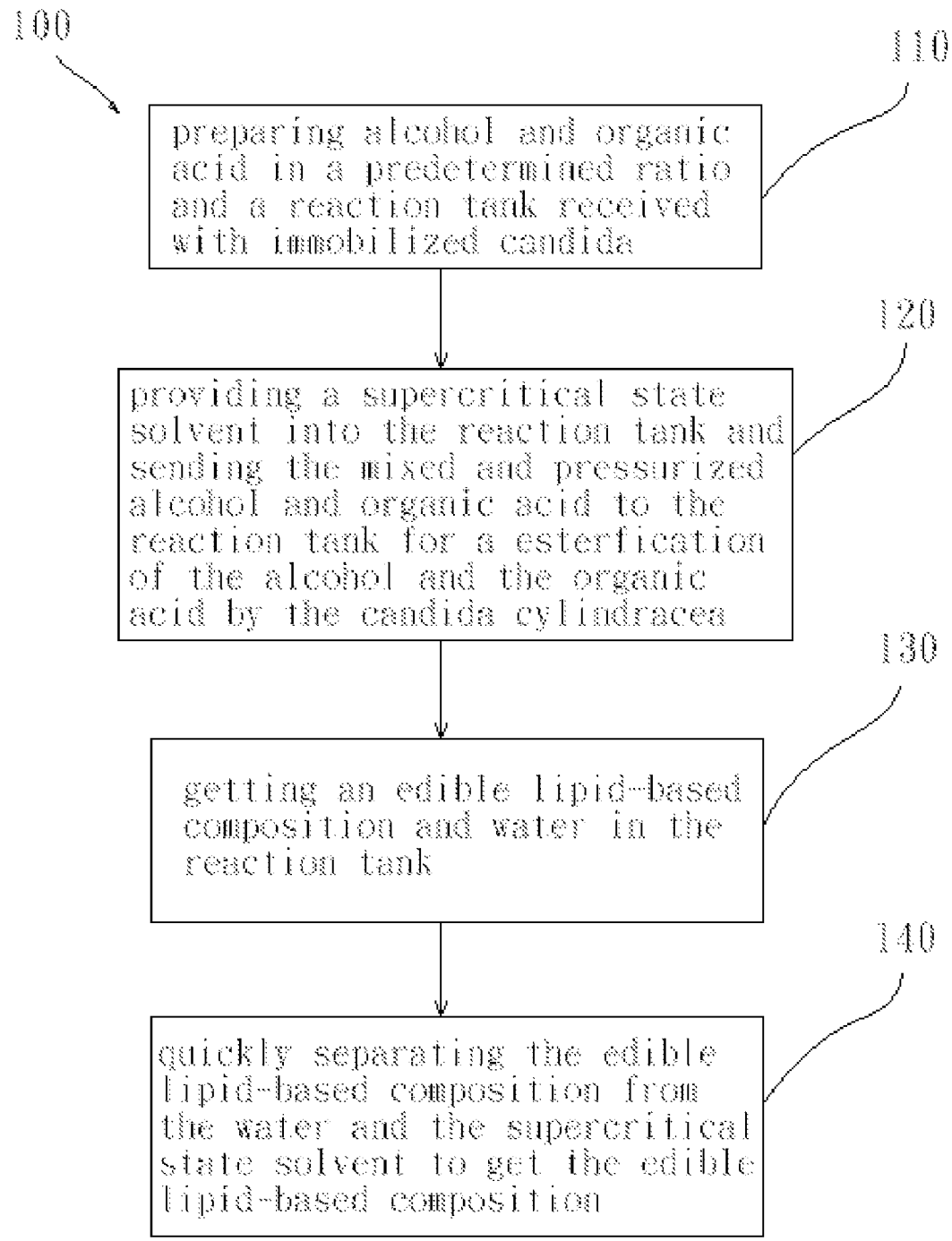
FIG. 1 is a flow chart of a preferred embodiment of the present invention.
Figure 2:
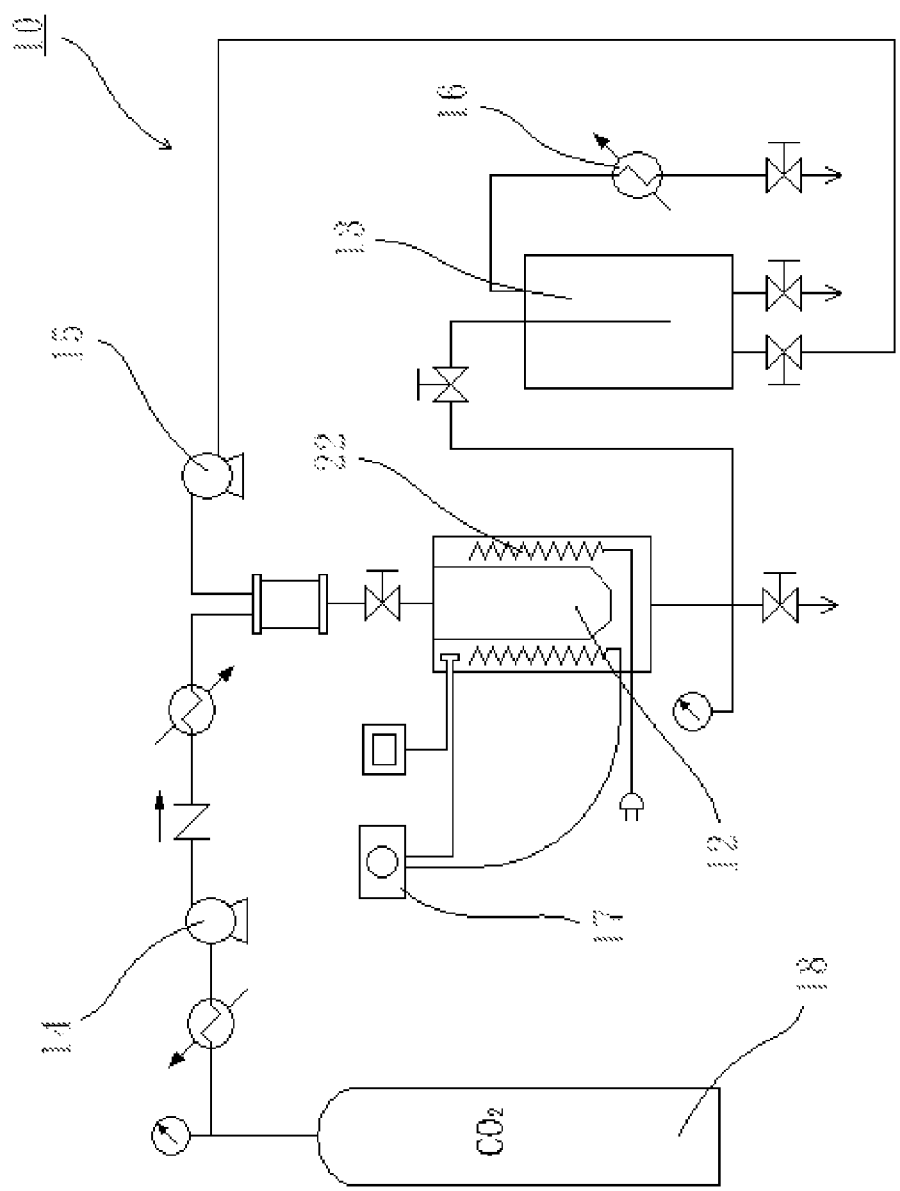
FIG. 2 is a sketch diagram of the synthesis system of the preferred embodiment of the present invention.

As shown in FIG. 1 and FIG. 2, a method 100 of the preferred embodiment of the present invention is for continuously producing edible lipid-based composition, such as alcohol, caffeic acid phenethyl ester (CAPE), and lipid, and the like. In the present invention, we take CAPE for example. The method 100 of the present invention uses supercritical fluid technique and a synthesis system 10 for continuous esterification. The synthesis system 10 includes a reaction tank 12, a separation tank 13, a high-pressure metering pump 14, a reactant metering pump 15, a cooler 16, a temperature controller 17, and a supercritical fluid container 18. The reaction tank 12 is provided with a thermocouple 22 therein. The separation tank 13 is connected to the reaction tank 12. The high-pressure metering pump 14 is connected to the supercritical fluid container. 18. The reactant metering pump 15 is connected to the reaction tank 12. The cooler 16 is connected to the separation tank 13. The temperature controller 17 is connected to the thermocouple 22. The supercritical fluid container 18 is a carbon dioxide steel bottle.

A first step 110 of the present invention is preparing alcohol and organic acid in a predetermined ratio, and providing immobilized *candida cylindracea* in the reaction tank 12. The alcohol is 2-phenyl-ethanol, and the organic acid is caffeic acid in a ratio of 1:10 in mole ratio. A weight of the *candida cylindracea* is 10 grams to 100 grams. The *candida cylindracea* is absorbed in a carrier of a hydrophobic member for immobilization. The reaction tank 12 is poured with water about 0.01~0.5 mL/min.

A second step 120 of the present invention is continuously providing a supercritical state solvent into the reaction tank 12 and draining it out, and mixing and pressurizing the alcohol and the organic acid and putting them into the reaction tank 12 that the alcohol and the organic acid occur esterification in the reaction tank 12. The supercritical state solvent is carbon dioxide under supercritical state ($SC-CO_2$). The high-pressure metering pump 14 pumps the supercritical state solvent into the reaction tank 12. The alcohol and the organic acid are mixed in the reactant metering pump 15, and the reactant metering pump 15 also serves the function of pressurizing the alcohol and the organic acid and pumping them into the reaction tank 12. The *candida cylindracea* helps esterification of the alcohol and the organic acid in the reaction tank 12.

The conditions of the synthesis system 10 include temperature: 40° C., pressure: 1000~3000 psia, concentration of the reactants: 0.1~5 mL/min, and the supercritical state solvent: 0.5~30 mL/min a preferred condition is temperature: 40±0.1° C., pressure: 2000~3000 psia, and the supercritical state solvent: 0.5 ml/min.

The esterification equation of the alcohol (2-phenyl-ethanol) and the organic acid (caffeic acid) is:

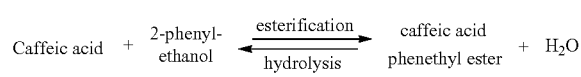

A third step 130 of the present invention is getting edible lipid-based composition and water in the reaction tank 12 after esterification. The esterification in the reaction tank 12 produces edible lipid-based composition (CAPE). After 72 hours, the conversion of edible lipid-based composition still is greater than 80%.

Above reaction is a reversible reaction. That is, CAPE will be hydrolyzed into 2-phenyl-ethanol, caffeic acid and ethyl alcohol. In general, speed of hydrolysis is much higher than esterfication. In order to raise the efficiency, a fourth step 140 of the present invention is quickly separating the edible lipid-based composition, water, and the supercritical state solvent to speed up esterfication. The products of the reaction are decompressed to take the edible lipid-based composition out in order to quickly separate the supercritical state solvent and the edible lipid-based composition.

The supercritical fluid container 18 is opened first, and then the high-pressure metering pump 14 is adjusted to a preset pressure and the temperature controller 17 in the reaction tank 12 to a best temperature for *candida cylindracea*. Next, start the reactant metering pump 15 for a predetermined flow rate of reactant (the ratio of the alcohol and the organic acid is 1:10 in mole ratio) to pump the alcohol and the organic acid into the reaction tank 12 for esterfication. The products of reaction are sent to the separation tank 13 through the cooler 16, and the unreacted reactants are drained out of the separation tank 13.

The carbon dioxide under supercritical state is a solvent of esterfication with a low viscosity and high mass transfer. Except for esterfication, it may decompress to remove the products of reaction that may quickly separate the carbon dioxide under supercritical state and the product. Besides, it may add water in the reaction tank 12 to activate *candida cylindracea*. However, too much water will affect esterfication. A good control of water in the reaction tank 12 may enhance the activation of *candida cylindracea*. Immobilized *candida cylindracea* is reusable and may enlarge the contact area with reactants. It is very effective in esterfication and may increase mass transfer of the reactants and products in immobilized *candida cylindracea*.

A way of immobilizing *candida cylindracea* is dropping 6 grams *candida cylindracea* into 10° C., 120 ml ionized water, and adding 6 grams carrier, and then slowly adding 120 ml cool acetone. After *candida cylindracea* is precipitated, it is filtered by Whatman #1, and dried under 25° C. and 750 torr for 4~6 hours, and then *candida cylindracea* is stored under 0~5° C.

The analysis of the effects of water in the reactant on conversion and water removal on conversion of CAPE, and finding the base condition for synthesis of CAPE are describe hereunder.

Figure 3:
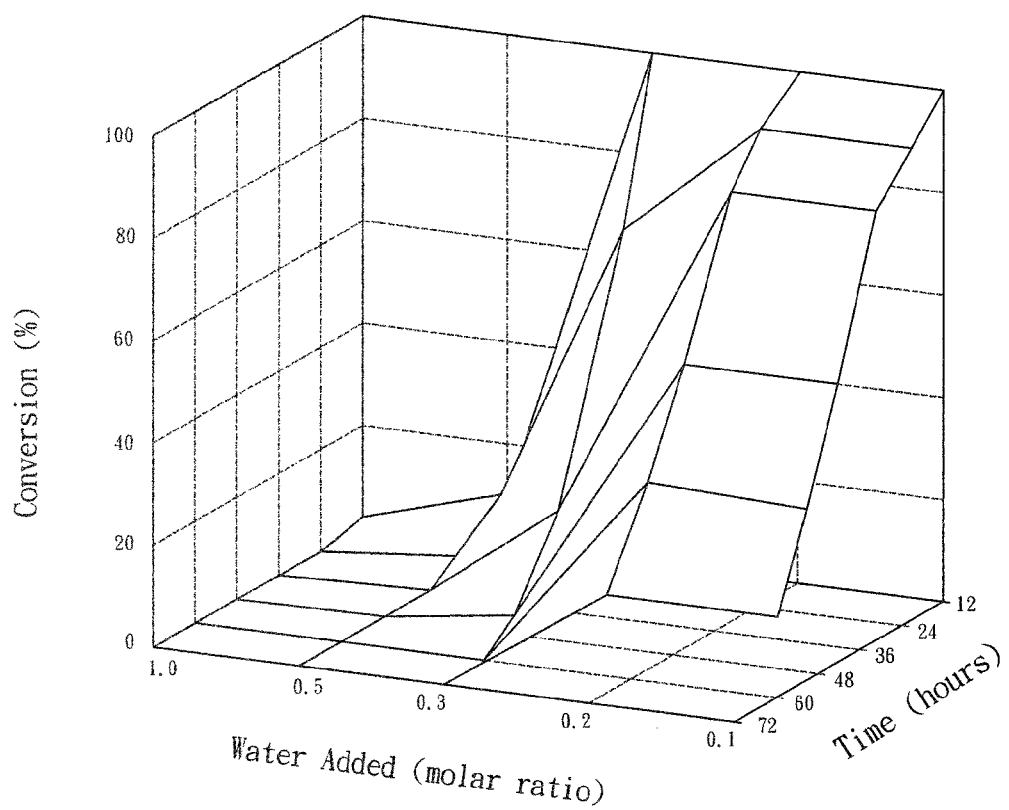
FIG. 3 is a diagram, showing the change of the conversion of water added in the reactant.

1. Effect of Water in the Reactant on Conversion:

Both of reactant and carrier will affect the conversion of lipid that how much water should be added may be found by experiment. The present inventor had proceeded semi-continuous esterfication for five days (12 hours per day), and found that the activation of immobilized *candida cylindracea* only has 10~20% left. After continuous reaction, the activation of *candida cylindracea* decreases or vanishes because that the reactants keep added into system and water of the products accumulated in system speed up hydrolysis to decrease the *candida cylindracea* remained in the system. In the best conditions for reaction recommended by the present invention (40° C., 2500 psia, 0.01 mL/min the reactant, 0.5 mL/min SC—$CO_2$, and 10 grams immobilized *candida cylindracea*), as shown on FIG. 3, a ratio of the organic acid (caffeic acid), the alcohol (2-phenyl-ethanol), and water is 1:10:0.1 or 1:10:0.2 in mole ratio may provide a good conversion for several days. Too much water will cause an overloading for *candida cylindracea* reaction and stops the reaction.

Figure 4:
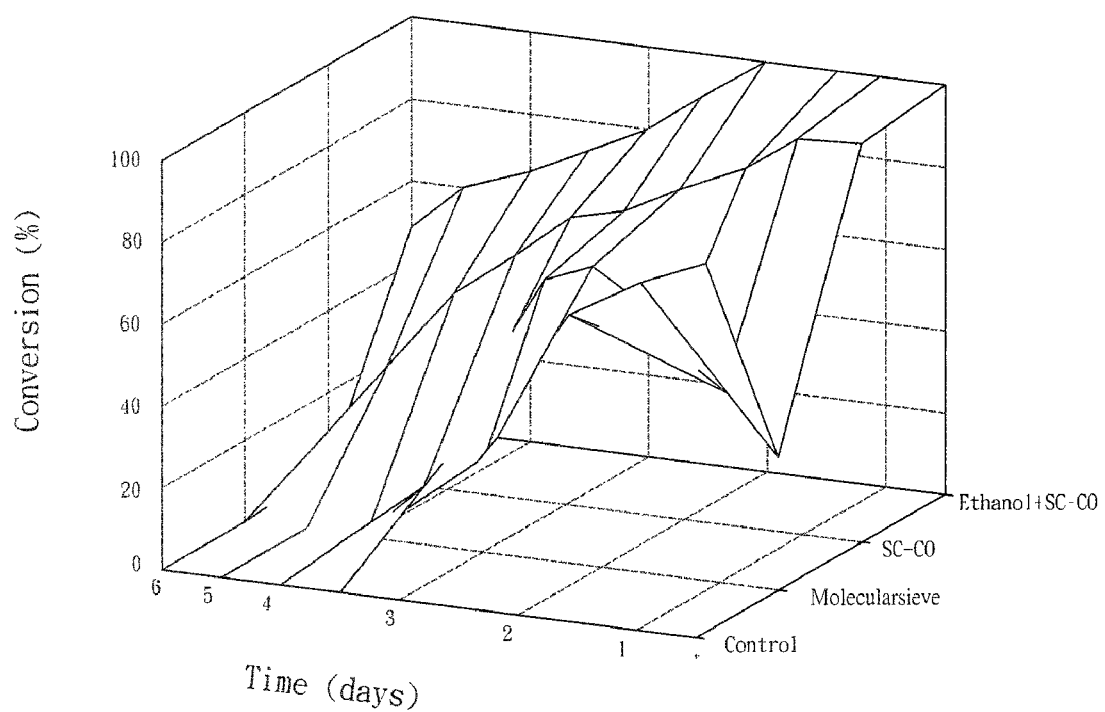
FIG. 4 is a diagram, showing the effect of water removal from the product on the conversion of CAPE.

2. Effect of Water Removal on Conversion of CAPE:

As shown in FIG. 4, after the water in the reaction tank is removed by ethyl alcohol and SC—$CO_2$, it may reduce the water of immobilized *candida cylindracea* in the reaction tank. It keeps the conversion over 50% after 6 days esterfication. Above water removal treatment and using unimmobilized *candida cylindracea* may extend the use of *candida cylindracea*. However, the best way is using the hydrophobic member to be the carrier of immobilized *candida cylindracea*.

Figure 5:
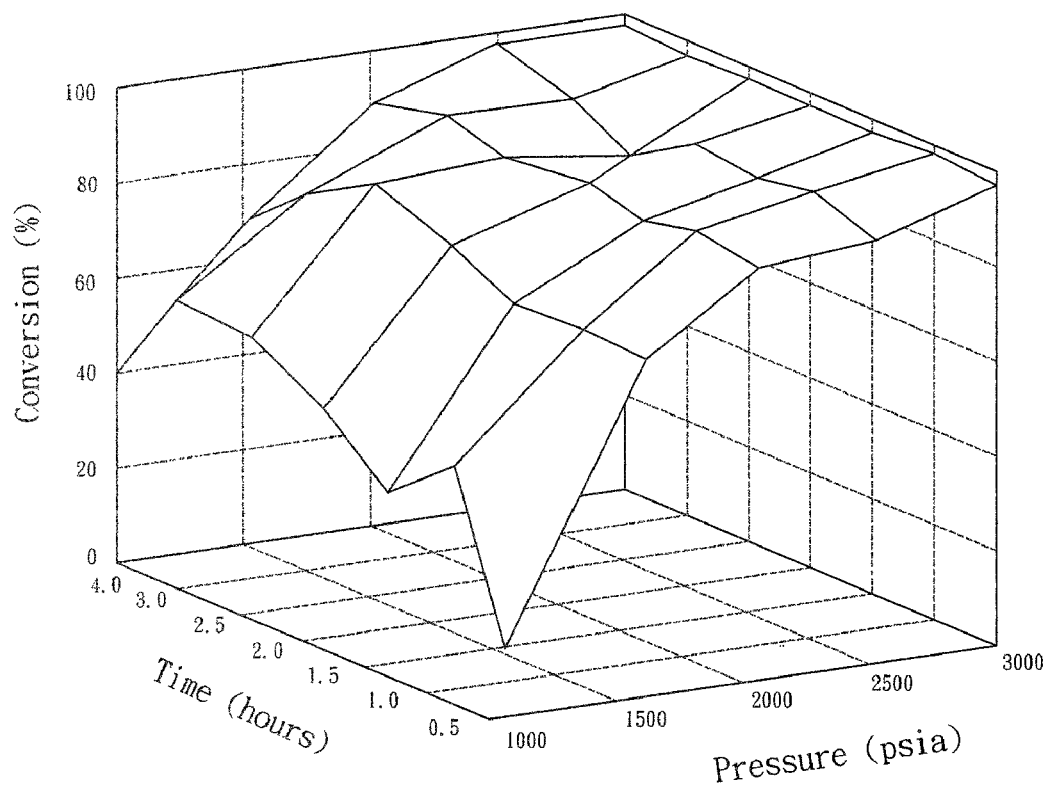
FIG. 5 is a diagram, showing the change of conversion under various pressures.

3. Finding the Best Condition for Synthesis of CAPE:

As shown FIG. 5, after the sample is esterficated in the reaction tank, the conversion of CAPE is over 80%. The best condition for esterfication is 40° C. and 2000~3000 psi. The main reason is that the reactant and SC—$CO_2$ under 2000~3000 psi has the greatest density and enhances the reactant in contact with *candida cylindracea*. In other words, the reactant and SC—$CO_2$ have a great chance in contact with *candida cylindracea* in a unit volume to speed up esterfication and raise the conversion thereof.

With the method of the present invention, the esterfication using supercritical fluid technique and *candida cylindracea* may synthesize the organic acid (caffeic acid), the alcohol (2-phenyl-ethanol) to edible lipid-based composition (CAPE). In comparison with the conventional method, the present invention provides a high speed esterfication. Besides, the present invention is cheaper than the conventional method, and no solvent residual. It costs about four New Taiwan Dollars for making 20 mg/mL CAPE solution by the method of the present invention.

In conclusion, the method of the present invention may continuously producing edible lipid-based composition, such as alcohol, CAPE, and lipid in a short time. No poison solvent is involved and no solvent is remained. The cost is low to practice in mass production.

The description above is a few preferred embodiments of the present invention and the equivalence of the present invention is still in the scope of claim construction of the present invention.

What is claimed is:

1. A method of continuously producing edible lipid-based composition, comprising the steps of:
   a) preparing alcohol and organic acid in a predetermined ratio and a reaction tank received with immobilized *candida cylindracea*;
   b) continuously providing a supercritical state solvent into the reaction tank and draining the supercritical state solvent out, and mixing and pressurizing the alcohol and the organic acid and sending the alcohol and the organic acid to the reaction tank for a esterfication of the alcohol and the organic acid by the *candida cylindracea*;
   c) getting an edible lipid-based composition and water in the reaction tank; and
   d) quickly separating the edible lipid-based composition from the water and the supercritical state solvent.

2. The method as defined in claim 1, wherein the alcohol is 2-phenyl-ethanol, and the organic acid is caffeic acid in the step a.

3. The method as defined in claim 2, wherein the ratio of 2-phenyl-ethanol and the caffeic acid is 1:10 in mole ratio in the step a.

4. The method as defined in claim 1, wherein the *candida cylindracea* is absorbed in a carrier for immobilization.

5. The method as defined in claim 4, wherein the carrier is a hydrophobic member.

6. The method as defined in claim 4, further comprising adding water in the reaction tank in the step a.

7. The method as defined in claim 6, wherein a weight of the *candida cylindracea* is in a range between 10 grams and 100 grams, and the water is in a range between 0.01 mL/min and 0.5 mL/min.

8. The method as defined in claim 1, wherein the supercritical state solvent is carbon dioxide under supercritical state.

9. The method as defined in claim 1, wherein a temperature in the reaction tank is 40±0.1° C. and a pressure is a range between 2000 psia and 3000 psia, and a weight of the supercritical state solvent is in a range between 0.1 grams and 0.3 grams.

10. The method as defined in claim 1, wherein the edible lipid-based composition is caffeic acid phenethyl ester in the step c.

11. The method as defined in claim 1, wherein decompressing a pressure in the reaction tank to separate the edible lipid-based composition from the supercritical state solvent.

* * * * *